US00PP26320P2

(12) United States Plant Patent
Smith

(10) Patent No.: US PP26,320 P2
(45) Date of Patent: Jan. 19, 2016

(54) ***CHRYSANTHEMUM* PLANT NAMED 'CIFZ0023'**

(50) Latin Name: *Chrysanthemum×morifolium*
Varietal Denomination: CIFZ0023

(71) Applicant: Syngenta Crop Protection AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 128 days.

(21) Appl. No.: 13/998,267

(22) Filed: Oct. 17, 2013

(51) Int. Cl.
*A01H 5/00* (2006.01)

(52) U.S. Cl.
USPC ..... Plt./288

(58) Field of Classification Search
USPC ..... Plt./288
See application file for complete search history.

*Primary Examiner* — Keith Robinson
(74) *Attorney, Agent, or Firm* — Joshua L. Price

(57) ABSTRACT

A new *Chrysanthemum* plant named 'CIFZ0023' particularly distinguished by the medium sized pure white decorative inflorescences, medium sized plant habit with a rounded and mounded habit, and a natural season flowering response of early October.

1 Drawing Sheet

Latin name of the genus and species of the plant claimed: *Chrysanthemum×morifolium.*

Varietal denomination: 'CIFZ0023'.

BACKGROUND OF THE NEW PLANT

The present invention comprises a new *Chrysanthemum,* botanically known as *Chrysanthemum×morifolium,* and hereinafter referred to by the variety name 'CIFZ0023'.

'CIFZ0023' is a product of a planned breeding program. The new cultivar has medium sized pure white decorative inflorescences, medium sized plant habit with a rounded and mounded habit, and a natural season flowering response of early October.

'CIFZ0023' originated from a hybridization made in January 2008 in a greenhouse in Tenjo, Columbia. The female parent was the proprietary patented plant designated 'Yoalexis', U.S. Plant Pat. No. 15,318, with creamy white inflorescence color and a taller plant habit in natural season crops, with a lighter green foliage that is less likely to turn yellow in cool growing crops when compared to 'CIFZ0023'.

The male parent of 'CIFZ0023' was the unpatented, proprietary plant designated as '03-M342' with yellow inflorescences and more disk florets, smaller overall plant size and a natural season flowering response that is up to four weeks faster when compared to 'CIFZ0023'. The resultant seed was sown and grown outdoors in June 2009 in Alva, Fla. USA.

'CIFZ0023' was selected as one flowering plant within the progeny of the stated cross in November 2009 in Alva, Fla.

The first act of asexual reproduction of 'CIFZ0023' was accomplished when vegetative cuttings were propagated from the initial selection in January 2010 in a greenhouse in Alva, Fla.

BRIEF SUMMARY OF INVENTION

Horticultural examination of plants grown from cuttings of the plant initiated in January 2010, and continuing thereafter, has demonstrated that the combination of characteristics as herein disclosed for 'CIFZ0023' are firmly fixed and are retained through successive generations of asexual reproduction.

'CIFZ0023' has not been observed under all possible environmental conditions. The phenotype may vary significantly with variations in environment such as temperature, light intensity, and day length.

A Plant Breeder's Right for this cultivar was applied for in Canada on Mar. 8, 2013, No. 13-7958. 'CIFZ0023' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0023' with colors being as true as possible with an illustration of this type.

The photographic drawing shows a flowering plant of the new variety and a close-up of the inflorescences.

DETAILED BOTANICAL DESCRIPTION

The plant descriptions, measurements and aforementioned photographs were taken in Gilroy, Calif. in August outdoors under natural light from plants that were about 11 weeks old. These plants were grown in 6 inch pots in a greenhouse trial under blackcloth conditions. These plants were not pinched.

Color references are made to The Royal Horticultural Society Colour Chart (R.H.S.) 2001.

TABLE 1

DIFFERENCES BETWEEN THE NEW VARIETY 'CIFZ0023' AND A MOST SIMILAR VARIETY

| | 'CIFZ0023' | 'Lesconil' (U.S. Plant Pat. No. 22,832) |
|---|---|---|
| Inflorescence color: | More pure white | Less creamy |
| Inflorescence size: | Little larger | Little smaller |
| Foliage color: | Darker green | Lighter green |
| Plant size: | Bit larger overall | Bit smaller overall |

Plant:

*Form, growth and habit*.—Herbaceous garden-type, stems upright and outwardly spreading, freely branching, strong and moderately vigorous growth habit.

*Plant height*.—16-18.0 cm.

*Plant height* (*inflorescence included*).—19-21.0 cm.

*Plant width*.—31-34.0 cm.

*Plant growth rate*.—Average.

Roots:

*Number of days to initiate roots*.—About 4-6 days at about 22 degrees C.

*Number of days to produce a rooted cutting*.—About 14-16 days at 22 degrees C.

*Type*.—Fine, fibrous, free branching.

*Color*.—RHS N155B.

Foliage:

*Arrangement*.—Alternate.

*Immature, leaf color, upper surface*.—Closest to RHS 147A.

*Immature, leaf color, lower surface*.—RHS 147B but appears lighter due to hairs.

*Mature, leaf color, upper surface*.—Closest to RHS 147A.

*Mature, leaf color, lower surface*.—RHS 147B but appears lighter due to hairs.

*Length*.—3.7-4.8 cm.

*Width*.—2.0-2.2 cm.

*Shape*.—Ovate.

*Base shape*.—Attenuate.

*Apex shape*.—Acute.

*Margin*.—Slightly palmately lobed, slightly dentate.

*Texture, upper surface*.—Bifid T-shaped hairs.

*Texture, lower surface*.—Bifid T-shaped hairs.

*Glossiness, upper surface*.—Weak.

*Glossiness, lower surface*.—Absent.

*Color of veins, upper surface*.—Closest to RHS 138B.

*Color of veins, lower surface*.—Closest to RHS 138A.

*Pattern of veining*.—Palmate.

*Petiole color*.—RHS 138B.

*Petiole attitude*.—Moderately upwards.

*Length*.—0.5 cm.

*Diameter*.—0.15-0.2 cm.

*Texture*.—Bifid T-shaped hairs.

Stem:

*Quantity of main branches per plant*.—About 10.

*Color of stem*.—RHS 137B but appears lighter due to hairs.

*Length of stem*.—9-11.0 cm.

*Strength of stem*.—Average.

*Diameter*.—0.3-0.4 cm.

*Length of internodes*.—0.5-1.0 cm.

*Texture*.—Bifid T-shaped hairs.

*Color of peduncle*.—Closest to RHS 137B.

*Length of peduncle*.—3-3.5 cm.

*Peduncle diameter*.—0.25 cm.

*Aspect of peduncle*.—Upright.

*Strength of peduncle*.—Average.

*Texture*.—Bifid T-shaped hairs.

Inflorescence:

*Type*.—Compositae, solitary decorative-type, inflorescences borne terminally above foliage, ray florets arranged acropetally on a capitulum.

*Quantity of short days to flowering* (*response time*).—About 7 weeks.

*Natural season flowering*.—Early October.

*Quantity of inflorescences per plant*.—About 75 showing some color, with about 25 more buds.

*Lastingness of individual blooms on the plant*.—About 6 weeks from first color.

*Fragrance*.—Slightly spicy.

*Corolla tube diameter and length*.—Small and hidden within the flower cluster.

Bud (just when opening/showing color):

*Color*.—Closest to RHS 155A.

*Length*.—0.7-0.9 cm.

*Width*.—0.7 cm.

*Shape*.—Oblate.

Immature inflorescence:

*Diameter*.—4-5.0 cm.

*Color of ray florets, upper surface*.—Closest to RHS 155A.

*Color of ray florets, lower surface*.—Closest to RHS 155A.

Mature inflorescence:

*Diameter*.—5-5.4 cm.

*Depth*.—1.5-1.7 cm.

*Total diameter of disc*.—None showing at this time.

*Receptacle color*.—RHS 145C.

*Receptacle height*.—0.3 cm.

*Receptacle diameter*.—0.4 cm.

Ray florets:

*Average quantity of florets*.—130-150 in several whorls.

*Orientation*.—Horizontal to slightly upwards.

*Color of florets, upper surface*.—Closest to N155D but more pure white.

*Color of florets, lower surface*.—Closest to N155D but more pure white.

*Length*.—2.4-2.7 cm.

*Width*.—0.6-0.8 cm.

*Shape*.—Elliptical.

*Apex shape*.—Praemorse.

*Base shape*.—Attenuate.

*Margin*.—Entire.

*Texture, upper surface*.—Papillose.

*Texture, lower surface*.—Papillose.

Disc florets:

*Average quantity of florets*.—About 10-14.

*Color of florets*.—RHS 1C base with RHS 1B apex.

*Length*.—0.2 cm.

*Width*.—0.5 cm.

*Shape*.—Tubular, elongated.

*Apex shape*.—Acute, 5 pointed.

*Texture, inner surface*.—Glabrous.

*Texture, outer surface*.—Glabrous.

Phyllaries:

Quantity.—20-25; 1 outer row of about 8 distinctly larger ones and numerous smaller inner ones.

*Larger, color, upper surface*.—Closest to RHS 147A.

*Lower surface*.—Between RHS 137A and RHS 137B.
*Length*.—1.3-1.5 cm.
*Width*.—0.25-0.3 cm.
*Shape*.—Lanceolate.
*Apex shape*.—Acute.
*Base*.—Fused.
*Margins*.—Entire.
*Smaller, color, upper surface*.—RHS 146B.
*Lower surface*.—RHS 146A.
*Length*.—0.6-0.8 cm.
*Width*.—0.15-0.2 cm.
*Shape*.—Lanceolate.
*Apex shape*.—Acute.
*Base*.—Fused.
*Margins*.—Entire but papery.
*All phyllaries, texture, upper surface*.—Glabrous.
*Lower surface*.—Bifid T-shaped hairs.

Reproductive organs:

*Pistil*.—1, found on both types of florets.
*Length*.—0.2 cm.
*Style color*.—RHS 1C and more translucent looking.
*Style length*.—0.125 cm.
*Stigma color*.—RHS 1B.
*Stigma shape*.—Bi-parted.
*Ovary*.—All very undeveloped, could not take any data.
*Stamens*.—4, found on only on the disc florets.
*Color of filaments*.—RHS 155C.
*Length filaments*.—0.2 cm.
*Anther color*.—RHS 14A.
*Anther length*.—0.15 cm.
*Anther shape*.—Oblong.
*Color of pollen*.—RHS 17B.
*Pollen amount*.—Sparse.
*Fertility/seed set*.—Has not been observed to date.
*Disease/pest resistance*.—Has not been observed to date.

What is claimed is:

1. A new and distinct variety of *Chrysanthemum* plant named 'CIFZ0023' substantially as illustrated and described herein.

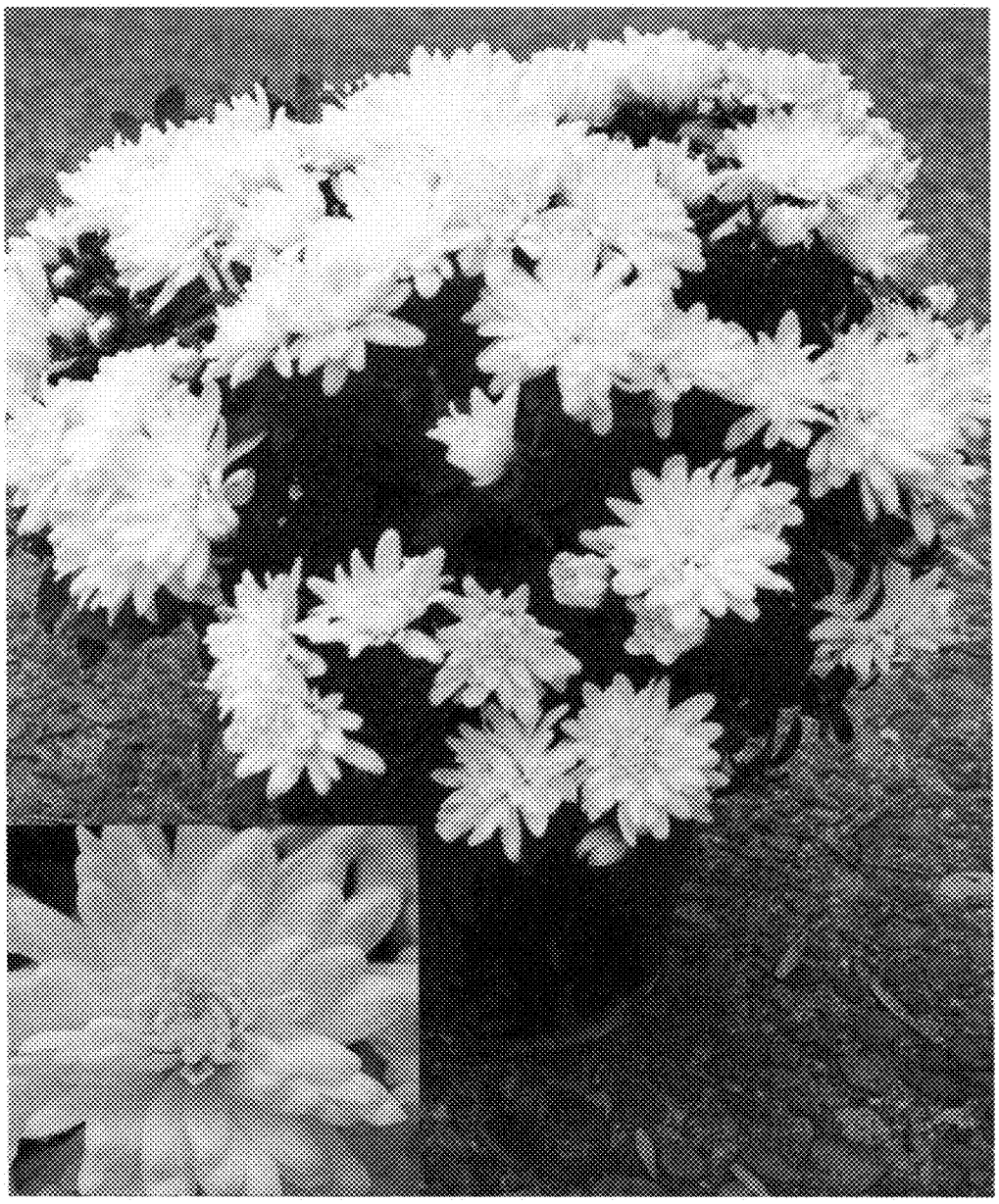

* * * * *